(12) United States Patent
Schumacher et al.

(10) Patent No.: US 9,318,885 B2
(45) Date of Patent: Apr. 19, 2016

(54) PROTECTIVE SHEATH DEVICE WITH MOUNTING PIECE FOR LEAD WIRE CABLES

(71) Applicant: Medashield Technologies, LLC, Corsicana, TX (US)

(72) Inventors: Joshua T. Schumacher, Fort Worth, TX (US); Peter S. Mileski, Frisco, TX (US)

(73) Assignee: MEDASHIELD TECHNOLOGIES, LLC, Corsicana, TX (US)

( * ) Notice: Subject to any disclaimer, the term of this patent is extended or adjusted under 35 U.S.C. 154(b) by 225 days.

(21) Appl. No.: 14/073,730

(22) Filed: Nov. 6, 2013

(65) Prior Publication Data

US 2014/0131066 A1    May 15, 2014

Related U.S. Application Data

(60) Provisional application No. 61/877,251, filed on Sep. 12, 2013, provisional application No. 61/724,500, filed on Nov. 9, 2012.

(51) Int. Cl.
| | | |
|---|---|---|
| *H02G 3/04* | (2006.01) | |
| *H02G 1/00* | (2006.01) | |
| *A61B 19/08* | (2006.01) | |

(52) U.S. Cl.
CPC ............ *H02G 3/0462* (2013.01); *A61B 19/081* (2013.01); *H02G 1/00* (2013.01); *A61B 2562/247* (2013.01); *Y10T 29/49826* (2015.01)

(58) Field of Classification Search
CPC ............................. H02G 3/0462; A61B 19/081
USPC .................................. 174/135, 103; 607/116
See application file for complete search history.

(56) References Cited

U.S. PATENT DOCUMENTS

| | | |
|---|---|---|
| 3,698,791 A | 10/1972 | Walchle et al. |
| 4,723,912 A | 2/1988 | Nieusma |

(Continued)

FOREIGN PATENT DOCUMENTS

WO     2010/047703     4/2010

OTHER PUBLICATIONS

European Patent Office; International Search Report and Written Opinion; PCT Application No. PCT/US2013/068802; Feb. 24, 2014.

*Primary Examiner* — William H Mayo, III
*Assistant Examiner* — Hiram E Gonzalez
(74) *Attorney, Agent, or Firm* — Jackson Walker LLP

(57) ABSTRACT

A protective sheath device for use in protecting lead wire cables from contamination during use in a hospital or other medical setting is described. A glove-like component having fingers, with each finger intended to protect one lead wire, is placed on a base or mounting piece. The base has extensions that fit within the fingers, and the fingers are gathered to reduce their length. This facilitates placement of a lead wire cable within each finger. Once the cables are placed within the fingers of the glove-like component, the base can be discarded and the terminal heads of the lead wire cables are grasped and pulled to extend the fingers of the glove-like component and to protect a length of the lead wire cables. If the base is a mounting piece, it is preferably retained for later uses and is made of a material such as rubber or plastic that can be sanitized and reused. The lead wire cable heads can be snapped directly onto sensor pads and will function through the material of the glove-like component, which is preferably a plastic. After use, the glove-like component is discarded and the lead wire cables and heads remain uncontaminated.

15 Claims, 8 Drawing Sheets

(56) References Cited

U.S. PATENT DOCUMENTS

| | | | | |
|---|---|---|---|---|
| 4,914,521 A * | 4/1990 | Adair | ............... | A61B 1/00142 348/375 |
| 8,155,755 B2 * | 4/2012 | Flynn | ............... | A61B 5/0002 174/103 |
| 8,662,456 B2 * | 3/2014 | Komiya | ............... | G02G 11/006 174/72 R |
| 2007/0044809 A1 | 3/2007 | Flynn et al. | | |
| 2012/0165621 A1 | 6/2012 | Grayzel et al. | | |

\* cited by examiner

PROTECTIVE SHEATH DEVICE WITH MOUNTING PIECE FOR LEAD WIRE CABLES

This application claims the benefit of U.S. Provisional Patent Application Ser. No. 61/724,500, entitled PROTECTIVE SHEATH DEVICE FOR LEAD WIRE CABLES filed on Nov. 9, 2012, and claims the benefit of U.S. Provisional Patent Application Ser. No. 61/877,251, entitled PROTECTIVE SHEATH DEVICE WITH MOUNTING PIECE FOR LEAD WIRE CABLES filed on Sep. 12, 2013, the entire content of each of which is hereby incorporated by reference.

BACKGROUND

The present disclosure pertains to devices and methods for providing a protective sheath for lead wire cables intended for use in hospital or medical settings, particularly ECG/EKG Multi-Link leadwire sets.

Hospital-acquired infections caused by antibacterial-resistant microorganisms are associated with high mortality and morbidity rates and markedly affect hospital economics. According to the Association for Professionals in Infection Control, one out of every 20 hospitalized patients in the United States contracts a Hospital Acquired Infection. This equates to 1.7 million patients infected annually, accounting for 99,000 deaths. The cost of treating patients with hospital-acquired infections ("HAIs") has increased markedly. Reports indicate that the cost of care of the 4% of patients with HAI wiped out 185% of the operating profits from all other patients. These numbers were generated before October 2008, when the Center for Medicare and Medicaid Services began to deny reimbursement for HAIs. Now that hospitals are no longer being reimbursed for selected HAIs, the loss of revenue is greater than ever before. The challenge to nurses and practitioners is to steer acute health care facilities to a course on which all measures that can prevent HAIs are identified and adopted, with a focus on eliminating the most costly infections, those caused by antibiotic-resistant bacteria.

Infections caused by cross-contamination with resistant bacteria can be eliminated by 3 methods: kill the bacteria before resistance develops, stop bacteria from communicating and acquiring resistance, and eliminate the pathway from one patient to another. The third method is particularly challenging due to the number of patients treated at health care facilities and the need to conserve and reuse resources and equipment between patients. Electrocardiography equipment is one example. Because electrocardiography equipment cannot be completely disinfected 100% of the time, it may be contributing to the growth of resistant bacteria. Reusable electrocardiography (ECG) wires, specifically the wire lead sets that connect the electrodes placed on a patient's chest to the trunk cable of a hardwired monitor or to a telemetry box, are a ubiquitous pathway for communication of HAIs caused by resistant organisms. ECG wires attached to even the least mobile patients can be found wrapped around endotracheal tubes, tracheostomy tubes, chest tubes, drains, urinary catheters, and so on, and the methods used to clean these reusable wires between patients is usually not effective enough to prevent cross-contamination of bacteria. A finding that reusable ECG wires carry and transport resistant bacteria after the wires are cleaned per hospital protocol was first reported in 2003 and again 5 years later in 2008. A multicenter study conducted in early 2009 also indicated that ECG wires were a potential source of HAI. A recent article in Cardiology News stated that antibiotic-resistant bacteria were found on 77% of ECG lead wires that were cultured after they were reprocessed and just before they were attached to new patients in the intensive care unit (ICU). The researcher, Dr. Paul R. Brookmeyer of the University of Wisconsin Hospital and Clinics, Madison was quoted as saying the wires are "'an unappreciated reservoir' of multidrug-resistant nosocomial pathogens." In addition, the article concluded that "attachment of contaminated lead wires to a new patient can result in colonization and ultimately in invasive infection by multiresistant nosocomial microorganisms."

ECG wires, identified as carriers of resistant strains of bacteria and an invasive infection risk, were thus linked directly to the root cause of cross-contamination infection in an article from the Division of Infectious Diseases at the University of Texas, Medical Branch in Galveston. The burn unit of that university hospital experienced "an outbreak of colonization and infection caused by vancomycin-resistant enterococci." Five weeks after the apparent eradication, the outbreak reoccurred. The reemergence of the infection was traced to one ECG lead wire. In addition to this account, Wisconsin hospital epidemiologists attributed an outbreak of *Serratia marcescens* infection to insufficiently decontaminated ECG leads. Unfortunately, these reports show that merely following a cleaning protocol for ECG wires is not sufficient to eliminate the risk of cross-contamination, even a cleaning protocol as rigorous as that expected from a burn unit attempting to eradicate an outbreak of vancomycin-resistant enterococci. Because of the nature of bacteria and the methods of development and transfer of antibiotic resistance, cleaning methods with bactericidal agents may be compounding the problem and contributing to the development of drug-resistant organisms.

Disposable electrocardiography leads might eliminate the risk of infection through these pathways. Adoption of disposable electrocardiography leads as an adjunct to an overall infection control program can decrease infection rates in acute health care facilities. However, there is a significant cost associated with the adoption of single-patient use disposable EKG Leads, especially in high patient "turnover" areas such as the OR, Procedural Areas, and ICU. What is needed is an alternate method for disinfecting or reusing lead wire cables that can be easily and inexpensively accomplished while still providing protection from cross-contamination between uses.

SUMMARY

The present disclosure pertains to a protective sheath device and methods for using the sheath device to protect lead wire cables from being contaminated during use. The protective sheath device is easily installed on the lead wire cables prior to use, preferably by using a specially designed mounting piece, and easily removed and discarded after use, while providing a barrier to contamination of the lead wires during use.

The protective sheath device described herein eliminates the path of infection from one patient to another by providing a single patient use disposable barrier between the EKG electrode and associated cabling/wires and the patient. After this barrier is used on one patient, it is to be removed and disposed of according to hospital protocol. Another barrier should be applied to the ECG cabling/electrode prior to application to the next patient.

The protective sheath device includes a base or a mounting piece and a glove-like component. The base or mounting piece holds the glove-like component while the lead wire cables are positioned within the fingers of the glove-like component. The fingers of the glove-like component can be gathered into accordion-like folds when placed on the base or mounting piece in order to facilitate easier placement of the lead wire cable heads at the ends of the fingers. The fingers of the glove-like component may then be extended to their full length to cover a portion of the lead wire cables as they are positioned for use. The base can be disposed of once the fingers are extended. The mounting piece is preferably retained for later uses. The heads of the lead wire cables are intended to attach directly to pads for placement on the patient and can do so even when placed within the fingers of the glove-like component.

The glove-like component of the protective sheath device is designed for single patient use only. This can be used in any hospital settings, doctor's offices, clinics, veterinarian clinics, and wherever there are leads that are attached to a person or animal that might be contaminated or infected during use. This device will preferably come in individual packaging intended for single use only and disposed after each use. The base is not necessary if the mounting piece is utilized. A kit could include the base and the glove-like component, with the glove-like component already installed on the base or separate.

DETAILED DESCRIPTION OF PREFERRED EMBODIMENTS

The protective sheath device described herein is made up of a glove-like component and a base or a mounting piece. The glove-like component has fingers that can be rolled up, compressed or scrunched into accordion-like folds to effectively shorten the length of the fingers. This compression of the fingers and the placement of the glove-like component on the base or mounting piece permits easy placement of lead wire cables, including heads on the ends of the cables, into the fingers of the glove-like component. Once the heads are placed into the fingers, preferably close to the ends of the fingers, the fingers can be extended and portions of the lead wire cables are effectively enclosed within and protected by the glove-like component. The lead wire cables can then be utilized as desired, including within a hospital or other medical facility to treat or monitor a patient. The heads of the lead wire cables can be attached or snapped directly onto the pads that will be placed on the patient while the heads are located within the glove-like component, as the material of the glove-like component is preferably a thin material that does not interfere with attachment or with monitoring.

Figure 1:
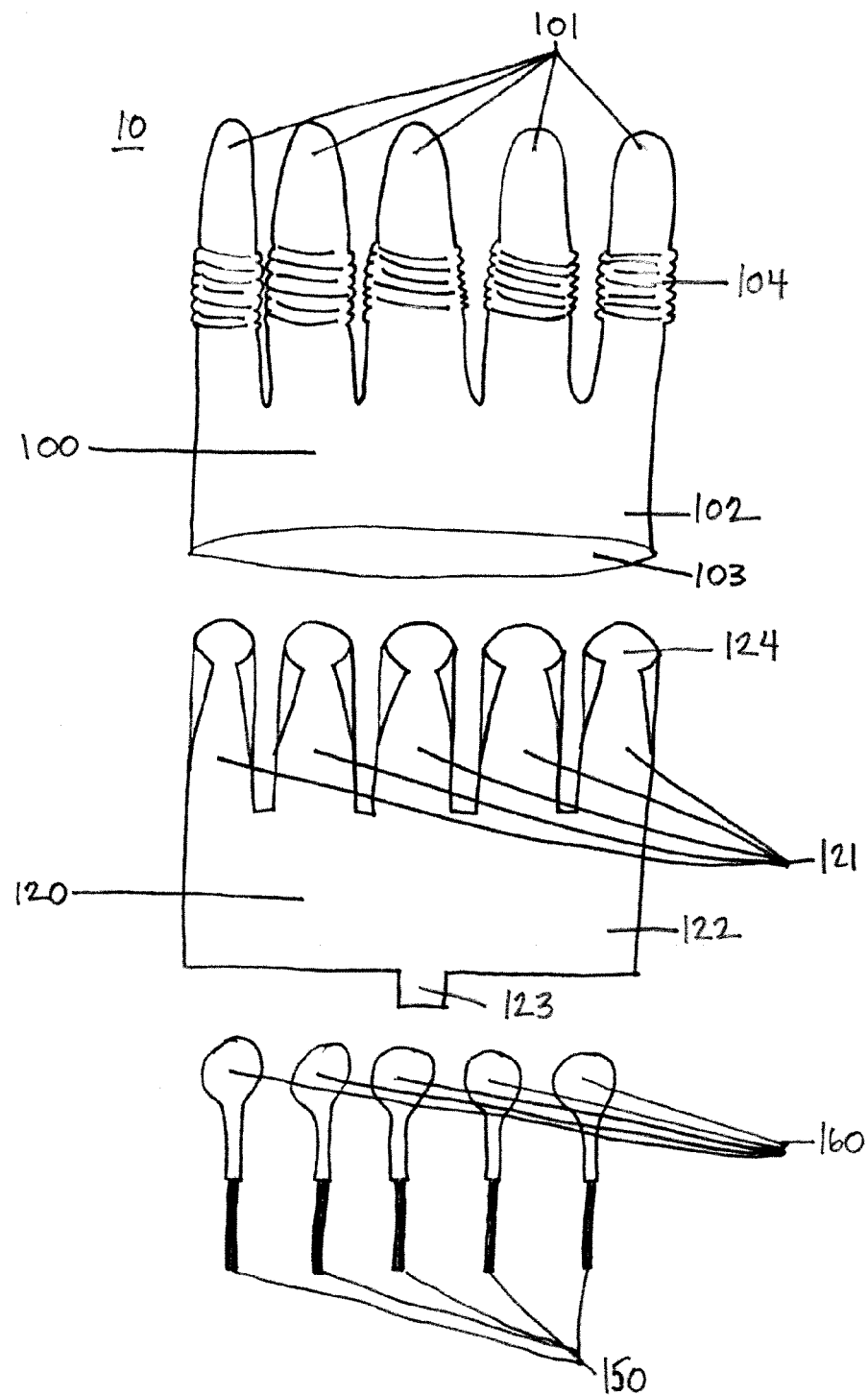
FIG. 1 shows an example of the protective sheath device in which an example of the glove-like component is separated from the base and the lead wire cables intended to be used with the protective sheath device are also illustrated separately.

FIG. 1 shows one example of a protective sheath device 10. The protective sheath device 10 includes a glove-like component 100 and a base 120. Lead wire cables 150 having lead wire cable heads 160 are also illustrated. The glove-like component 100 has fingers 101 which can be solid, serrated, or containing opening or perforation. In this particular example, the glove-like component 100 has five fingers 101, which correspond to the five lead wire cables 150. In other examples, the glove-like component might have 3, 6, 10, or 12 fingers, or as many needed to cover the number of lead wire cables being used. In this example, each finger 101 of the glove-like component 100 also contains a gathered portion 104 where the finger 101 has been gathered, rolled up or scrunched into accordion-like folds. Thus, the length of each finger 101 is actually longer than what is shown when the finger is fully extended and no longer gathered. The glove-like component also has a base open end 102 which can also be rolled, gathered, or scrunched into accordion-like folds, with an opening 103 that permits its placement onto the base 120. The opening 103 can be, if desired, closed with the use of tape, clip, clamp, or the like. The base 120 has extensions 121. In this particular example, the open end base 120 has five extensions 121 to correspond to the five fingers 101. In other examples, the base might have 3, 6, 10, or 12 extensions, or as many needed to correspond to the number of fingers 101 of the glove-like component 100. In this example, each extension 121 is shown to have a rounded end 124 that forms a rounded opening at the end of each extension 121, but the extensions 121 could also have flat ends. The base 120 also has a placement end 122 that may be easily grasped while positioning or removing the glove-like component 100 relative to the base 120. In this example, the base 120 also has a tab 123 that facilitates removal of the base 120 from the glove-like component 100.

Figure 2:
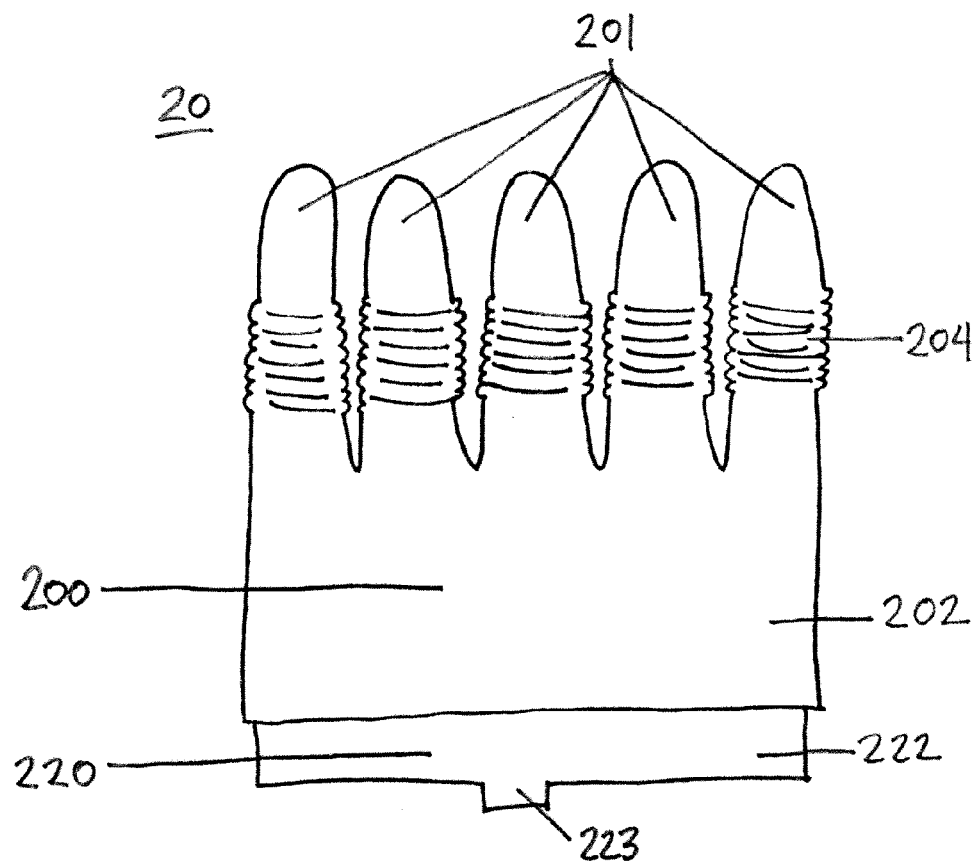
FIG. 2 shows an example of the protective sheath device in which an example of the glove-like component is positioned on the base.

FIG. 2 shows another example of a protective sheath device 20 in which the glove-like component 200 has been placed on the base 220. The extensions of the base, which are illustrated in FIG. 1 but not shown in FIG. 2, are placed or located within the fingers 201 of the glove-like component 200. The fingers 201 of the glove-like component 200 again each contain a gathered portion 204 where the finger 201 has been gathered, rolled up or scrunched into accordion-like folds. The base end 202 of the glove-like component also covers at least a portion of the placement end 222 of the base 220. In this example, a portion of the placement end 222 of the base 220 extends from the glove-like component 200 and has a tab 223 that facilitates easy removal of the base 220 from the glove-like component 200. The protective sheath device 20 may be packaged as it is shown in FIG. 2, with the base 220 placed within the glove-like component 200 and the fingers 201 scrunched to form each gathered portion 204.

Figure 3:
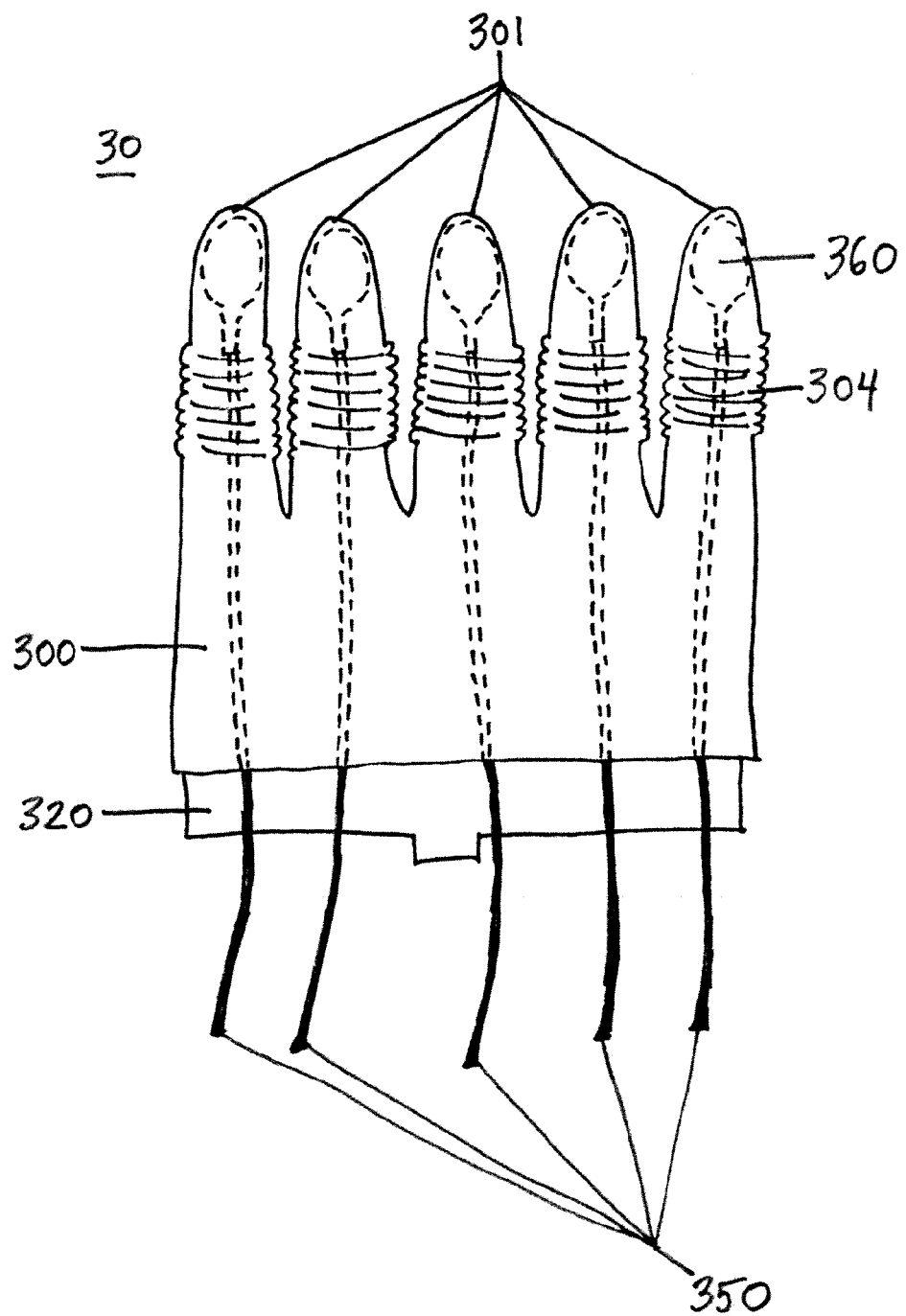
FIG. 3 shows an example of the protective sheath device in which an example of the glove-like component is positioned on the base and the heads of the lead wire cables and portions of the lead wire cables (shown in broken lines) are placed within the fingers of the glove-like component and other portions of the lead wire cables are illustrated extending out of the glove-like component.

FIG. 3 shows another example of a protective sheath device 30 which is substantially similar to the protective sheath device shown in FIG. 2. However, in FIG. 3, lead wire cables 350 have been placed within the fingers 301 of the glove-like component 300 while the glove-like component is located on the base 320. The portions of the lead wire cables 350, as well as each lead wire cable head 360, that are concealed within the glove-like component 300 are shown in broken lines. Although the extensions of the base 320 are not shown, they facilitate the placement of each lead wire cable head 360 and each lead wire cable 350 within the fingers 301 by stabilizing each finger. The rounded or flat ends of the extensions of the base 320 allow each lead wire cable head 360 to be fully passed into each finger 301. The gathered portion 304 of each finger 301 also more easily allows each lead wire cable head 360 to be fully passed into each finger 301 by eliminating the need to thread the lead wire cable 350 through the full length of each finger 301.

Figure 4:
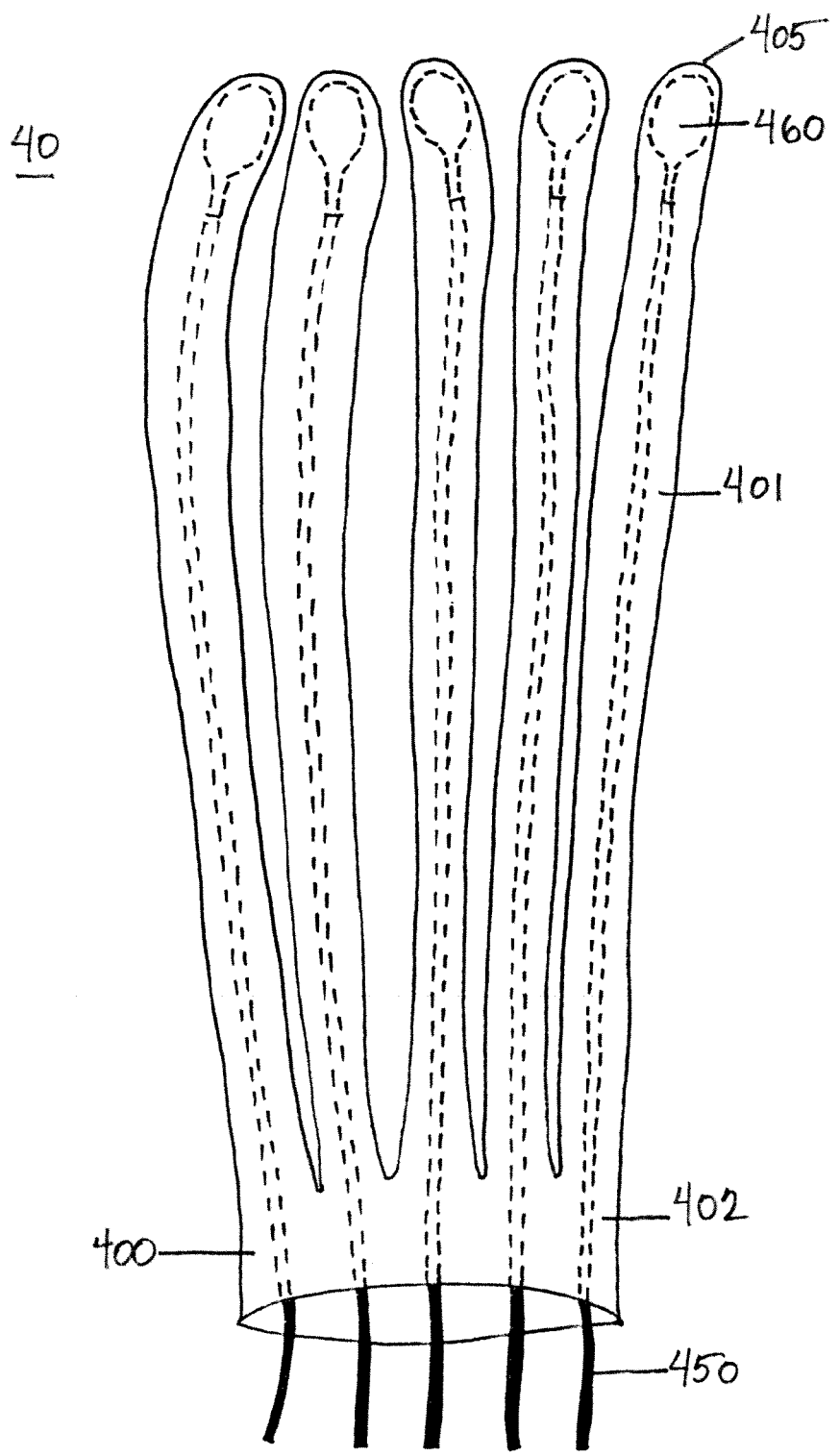
FIG. 4 shows an example of the protective sheath device in which the base has been disposed of, the fingers of the glove-like component have been extended, and the heads of the lead wire cables and portions of the lead wire cables (shown in broken lines) are shown within the fingers of the glove-like component while other portions of the lead wire cables are illustrated extending out of the glove-like component.

FIG. 4 shows another example of a protective sheath device 40 in which the base has already been removed from the glove-like component 400 and is not pictured. During actual use of the protective sheath device, the operative portion is the glove-like component. The base is intended primarily for ease of placement of the lead wire cables and is disposed of after placement of the lead wire cables within the glove-like component and prior to use. In FIG. 4, each finger 401 of the glove-like component 400 has been fully extended and has no gathered portion. Preferably, each finger 401 is extended after each lead wire cable head 460 is positioned at a terminal closed end 405 of each finger by grasping the lead wire cable head 460 within the finger 401 and pulling the terminal closed end 405 away from the base end 402 of the glove-like component 400. This draws the lead wire cable 450 further into the finger 401 until the finger 401 is fully extended. The length of the fingers 401 can vary depending on the length of the lead wire cables 450 that are in need of protection. After the fingers 401 are extended, the lead wire cable heads 460 can be snapped or attached onto the pad or other placement device intended to contact the patient. This attachment can be done through the fingers 401 of the glove-like component, which do not interfere with attachment or monitoring. In certain embodiments, a hole in a terminal closed end 405 of a finger 401 can be provided in order to facilitate attachment of the lead wire cable head 460 to a pad or placement device, but this embodiment provides a greater risk for contamination of the lead wire cable 450.

The glove-like component is preferably made of plastic and is thin enough not to interfere both with attachment of the lead wire cable heads to their respective pads or other external devices that contact the patient and with the monitoring of the patient. Accordingly, while the lead wire cables and lead wire cable heads are fully contained within the glove-like component, they can still be attached or snapped onto the pads or external devices. Different types of plastics that could be used for the glove-like component include:

PETE or PET (polyethylene terephthalate) marked with a Society of the Plastics Industry ("SPI") code of 1;
HDPE (high density polyethylene) marked with SPI code of 2;
PVC (Polyvinyl Chloride) marked with SPI code of 3;
LDPE (low density polyethylene) marked with SPI code of 4;
PP (polypropylene) marked with SPI code of 5;
PS (Styrofoam) marked with SPI code of 6; or
Miscellaneous plastics marked with SPI code of 7 (i.e., plastics not defined by SPI codes 1-6).

Figure 5:
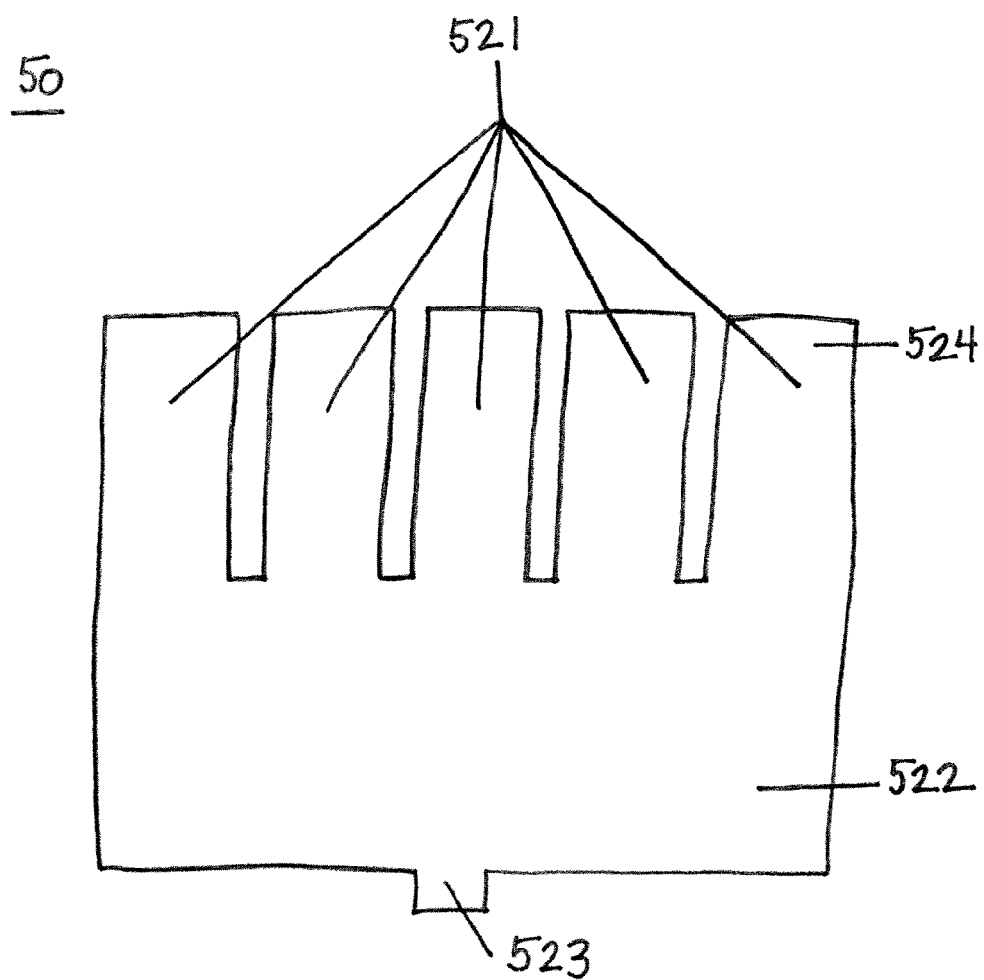
FIG. 5 shows an alternate example of the base of the protective sheath device without the glove-like component attached.

FIG. 5 shows an alternate example of a base 50 of the protective sheath device, without the glove-like component attached. The base 50 has extensions 521. In this particular example, the base 50 has five extensions 521 to correspond to a glove-like component having five fingers. In other examples, the base might have 3, 6, 10, or 12 extensions, or as many needed to correspond to the number of fingers of the glove-like component. In this example, each extension 521 is shown to have a flat end 524 rather than a rounded end. The base 50 also has a placement end 522 that may be easily grasped while positioning or removing the glove-like component relative to the base 50. In this example, the base 50 also has a tab 523 that facilitates removal of the base 50 from the glove-like component. The extensions 521 are fashioned so that they fit within the fingers of the glove-like component to stabilize the glove-like component while the lead wire cable heads and lead wire cables are being positioned within the fingers. The extensions 521 should stabilize the fingers without interfering with the placement of the lead wire cable heads and lead wire cables.

The base of the protective sheath device can be made of any suitably rigid yet flexible material, including disposable cardboard, plastic, or paper. The thickness of the base can vary and may be from about 1 mm to about 30 mm in thickness. The extensions of the base should be fashioned so they fit within the fingers of the glove-like component with which the base will be used, and the extensions can be flat or rounded on their ends.

In some embodiments of the protective sheath device, the glove-like component is used with a mounting piece instead of a base. While the base is intended to be disposed of after use, the mounting piece may preferably be retained for multiple uses. The mounting piece may be made of any suitably rigid yet flexible material that can be sanitized and re-used, such as natural or synthetic rubber, or plastics such as polyvinyl chloride (PVC), polyethylene, including polyethylene terephthalate, high density polyethylene, and low density polyethylene, or polypropylene.

Figure 6:
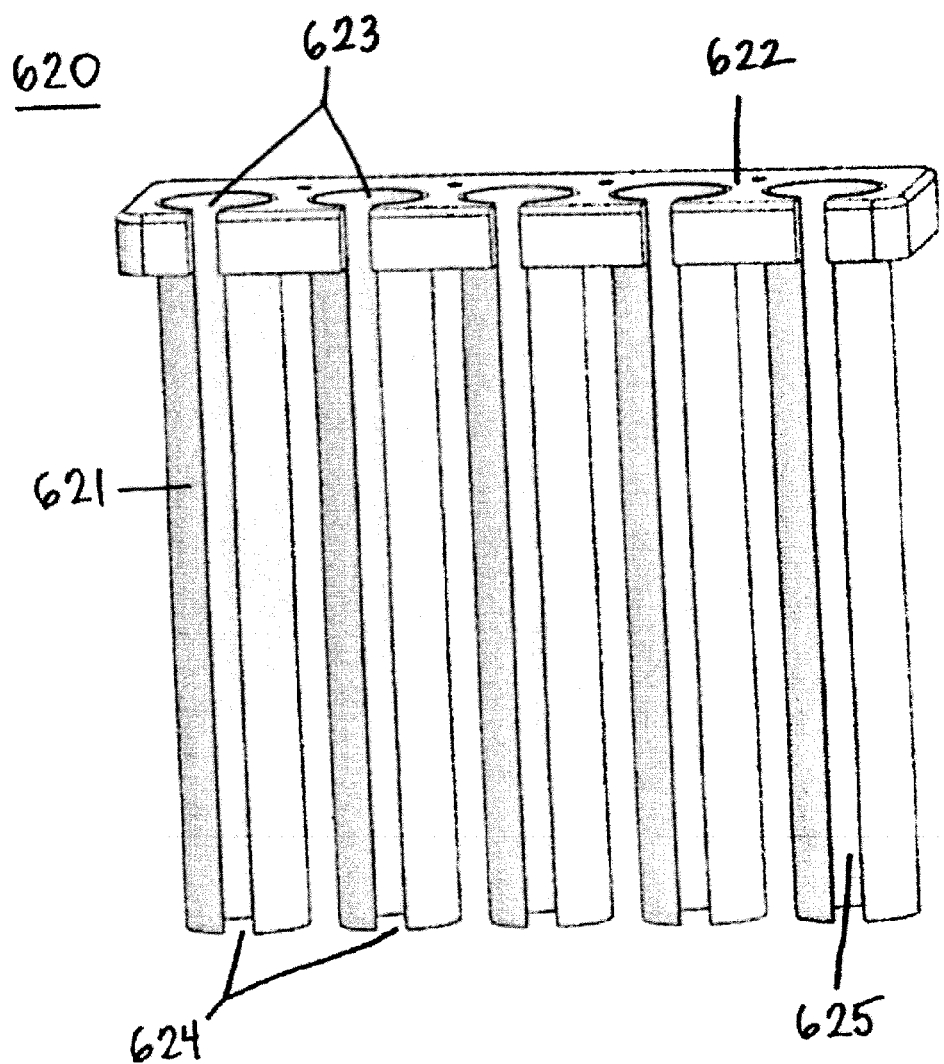
FIG. 6 shown an example of the mounting piece of the protective sheath device.

FIG. 6 shows one example of a mounting piece 620 for use with a glove-like component in a protective sheath device. Similar to the base seen in other examples, the mounting piece 620 has tubular extensions 621. In this particular example, the mounting piece 620 has five tubular extensions 621 that would correspond to a glove-like component having five fingers. In other examples, the base might have 3, 6, 10, or 12 extensions, or as many needed to correspond to the number of fingers of the glove-like component. In this example, each tubular extension 621 is shown to be generally rounded or tubular in shape. One end of each of the tubular extensions 621 is secured in a stabilizing end 622 of the mounting piece 620. The stabilizing end 622 connects to one end of each tubular extension 621 and stabilizes the tubular extensions 621 in a fixed position and distance relative to each other. Contained within the stabilizing end 622 are access openings 623 for each of the tubular extensions 621 to which the stabilizing end 622 is connected. In this example, each access opening 623 forms a rounded opening at the top of each tubular extension 621. At the bottom of each tubular extension 621 is also a passage opening 624 which is also rounded.

As seen in other examples with the extensions of the base, the tubular extensions 621 of the mounting piece 620 receive the fingers of a glove-like component, which surround the outside portion of each tubular extension. The access openings 623 of the mounting piece 620 allow for the entry of lead wire cable heads and lead wire cables, which are then passed through the tubular extensions 621 and through the passage openings 624 into the fingers of the glove-like component. Each tubular extension 621, access opening 623, and passage opening 624 also has a lead wire removal slit 625 which runs down the length of the tubular extensions 621. Once the lead wire cables have been passed through the tubular extensions 621 into the fingers of a glove-like component, the lead wire removal slit 625 allows for the removal of the glove-like component and any portion of lead wire cable extending out of the top of the glove-like component from the mounting piece 620. After use of the mounting piece 620 for loading lead wire cables into the fingers of a glove-like component, the mounting piece 620 is preferably retained for later uses.

Figure 7:
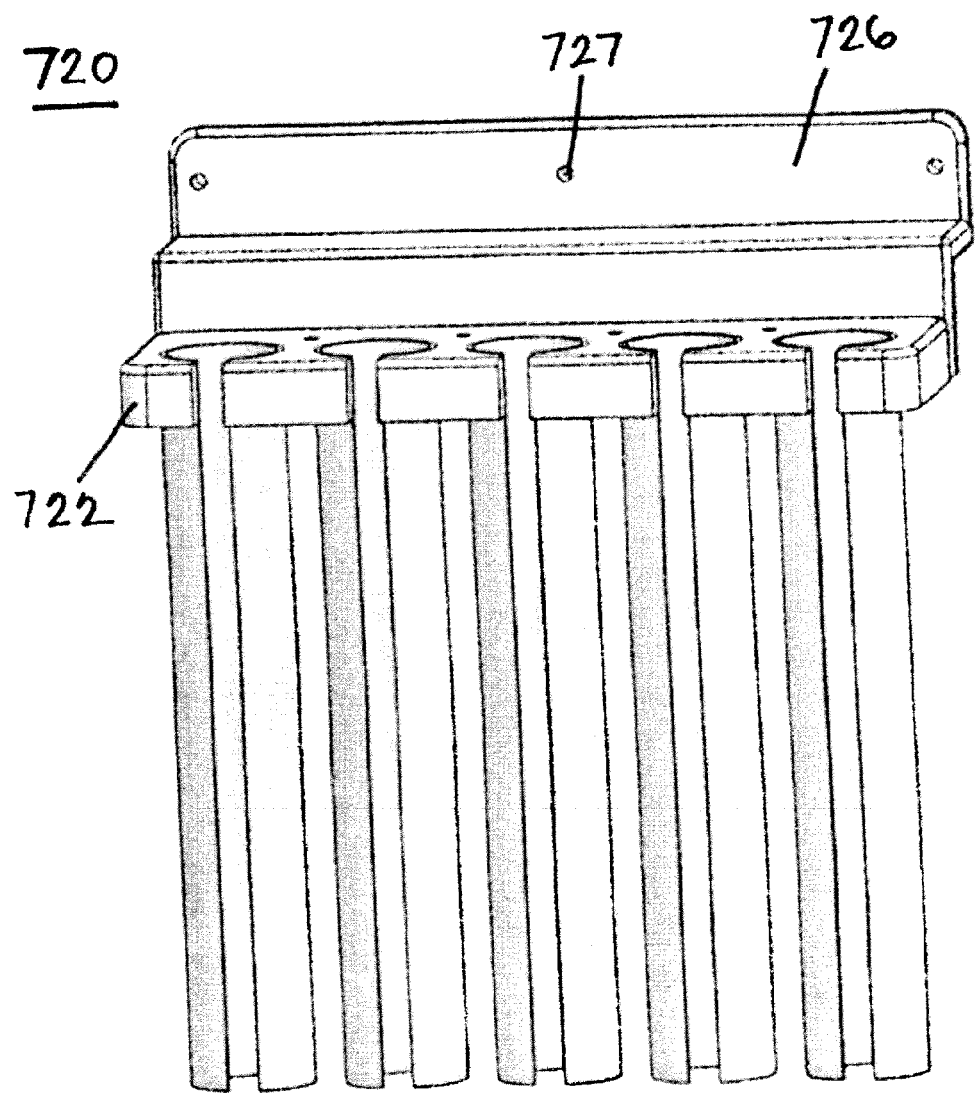
FIG. 7 shows an alternate example of the mounting piece of the protective sheath device including a bracket.

In some embodiments, the mounting piece 620 may be attached to a solid surface during use. This attachment preferably occurs at any portion of stabilizing end 622 that does not interfere with the ability to pass lead wire cable heads and lead wire cables into access openings 623 and out of lead wire removal slit 625, and also does not interfere with the ability to place the fingers of a glove-like component onto tubular extensions 621. The attachment may be permanent, though the use of fasteners like screws or nails, or temporary, through the use of fasteners such as hook and look fasteners. FIG. 7 shows an alternate example of a mounting piece 720 in which stabilizing end 722 is modified to include a bracket 726 for attachment to a wall or other surface. In this example, bracket 726 includes three attachment holes 727 to accommodate any fastener, including screws or nails, for attaching bracket 726 and mounting piece 720 to a surface.

Figure 8:
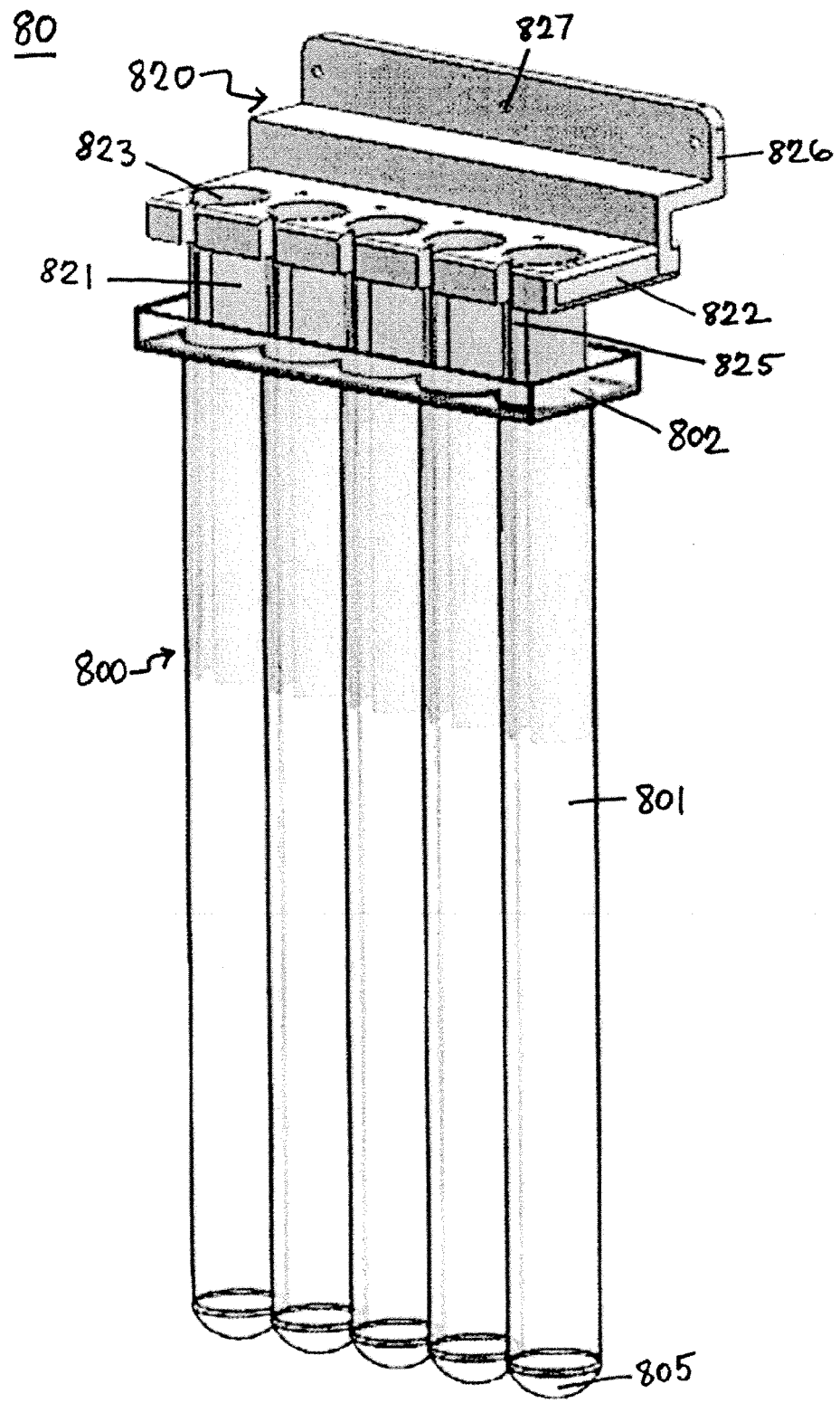
FIG. 8 shows an example of the mounting piece of the protective sheath device in which an alternate example of the glove-like component is positioned on the mounting piece.

FIG. 8 shows an example of a protective sheath device 80 including an example of a mounting piece 820 and an example of a glove-like component 800. Mounting piece 820 has tubular extensions 821 upon which fingers 801 of glove-like component 800 are placed. This example of a glove-like component 800 has a stabilizer open end 802 which is designed to engage with stabilizing end 822 of mounting piece 820. Once stabilizer open end 802 is placed on stabilizing end 822 and fingers 801 are passed over tubular extensions 821, lead wire cable heads and lead wire cables can be passed through access openings 823, through tubular extensions 821, into fingers 801, and through fingers 801 until terminal closed ends 805 of fingers 801 are reached. In FIG. 8, fingers 801 are not necessarily drawn to scale and may be significantly longer. In that case, fingers 801 may be partially gathered or rolled on tubular extensions 821 in order to make it easier for the lead wire cable heads to reach the terminal closed ends 805 of fingers 801. Once the lead wire cable heads and lead wire cables have been sufficiently placed within fingers 801, stabilizer open end 802 can be removed from stabilizing end 822 and fingers 801 can be removed from tubular extensions 821. Any remaining portions of lead wire cable extending through access openings 823 can easily be removed from the mounting piece 820 by passing them through lead wire removal slits 825. In this example, mounting piece 820 also contains bracket 826 and attachment holes 827 which would permit attachment of mounting piece 820 to a wall or flat surface so that it can be re-used.

A protective sheath device for protection of lead wire cables from contamination as described herein comprises a glove-like component having a number of fingers for receiving and protecting the lead wire cables and lead wire cable heads, wherein the fingers have terminal closed ends, and wherein the fingers have an extension length and a gathered length that is less than the extension length; and a base having a number of extensions for stabilizing the glove-like component while receiving the lead wire cables, wherein the glove-like component is adapted to be placed on the base prior to use to facilitate placement of the lead wire cables, wherein the fingers of the glove-like component are adapted to be placed on the extensions of the base to facilitate placement of the lead wire cables, wherein the fingers of the glove-like component are adapted to be gathered, rolled, or scrunched to facilitate placement of the lead wire cables, wherein when the fingers of the glove-like component are gathered the fingers have the gathered length to facilitate placement of the lead wire cables, wherein the fingers of the glove-like component are adapted to be extended to the extension length after placement of the lead wire cables and placement of the lead wire cable heads substantially within the terminal closed ends of the fingers, wherein the fingers are adapted to retain the lead wire cable heads substantially within the terminal closed ends and to retain the lead wire cables substantially throughout the extension length after extension, wherein the base is adapted to be removed after placement of the lead wire cables, and wherein the glove-like component protects the lead wire cables from contamination during use.

In certain embodiments of the protective sheath device, the number of fingers on the glove-like component is the same as the number of extensions on the base. In further embodiments, the extensions on the base are rounded or they are flat. The number of fingers on the glove-like components, as well as the number of extensions, can be 3, 5, 6, 10, or 12 in certain embodiments. In additional embodiments, the glove-like component is made of plastic. In certain embodiments of the protective sheath device, the plastic is a thickness that permits the lead wire cable heads to be attached to an external device while the lead wire cable heads are received in the glove-like component. The base is made of cardboard, plastic, or paper in further embodiments, and the base can have a thickness of about 1 mm to about 30 mm.

In certain additional embodiments of the protective sheath device, the base is a mounting piece made of rubber or plastic. In embodiments where the base is a mounting piece, the mounting piece may comprise a stabilizing end and the extensions of the base may be tubular. In additional embodiments, the stabilizing end may further comprise a bracket for attaching the mounting piece to a wall or other surface. The stabilizing end can also comprise access openings for each extension. The access openings and extensions can comprise a lead wire removal slit in further embodiments. In embodiments where the base is a mounting piece that comprises a stabilizing end, the glove-like component can also comprise a stabilizer open end adapted to engage with the stabilizing end of the mounting piece.

A method for protecting lead wire cables and lead wire cable heads from contamination described herein uses a protective sheath device, wherein the protective sheath device comprises a glove-like component having a number of fingers for receiving and protecting the lead wire cables and lead wire cable heads and a base having a number of extensions for stabilizing the glove-like component, and comprises the steps of: placing the glove-like component on the base and placing the fingers of the glove-like component on the extensions of the base to facilitate placement of the lead wire cables, wherein the fingers have terminal closed ends, and wherein the fingers have an extension length and a gathered length that is less than the extension length; gathering the fingers to the gathered length to facilitate placement of the lead wire cables; inserting lead wire cables having lead wire cable heads into the glove-like component, past the extensions of the base, and into the fingers of the glove-like component; placing the lead wire cable heads substantially within the terminal closed ends of the fingers; removing the base from the glove-like component; extending the fingers to the extension length while retaining the lead wire cable heads substantially within the terminal closed ends and retaining the lead wire cables substantially throughout the extension length; and using the lead wire cables, wherein the glove-like component protects the lead wire cables from contamination during use.

In certain embodiments of this method, the protective sheath device has a number of fingers on the glove-like component that is the same as the number of extensions on the base. In further embodiments, the extensions on the base are rounded or they are flat. The number of fingers on the glove-like components, as well as the number of extensions, can be 3, 5, 6, 10, or 12 in certain embodiments. In additional embodiments, the glove-like component is made of plastic. In certain embodiments of the protective sheath device, the plastic is a thickness that permits the lead wire cable heads to be attached to an external device while the lead wire cable heads are received in the glove-like component. In this embodiment, the method may further comprise the step of attaching the lead wire cable heads to an external device prior to the step of using the lead wire cables. The base is made of cardboard, plastic, or paper in further embodiments, and the base can have a thickness of about 1 mm to about 30 mm. In additional embodiments, the lead wire cables and lead wire cable heads are used in a medical or hospital setting, and in further embodiments, the lead wire cables and lead wire cable heads are ECG lead wire cables and ECG lead wire cable heads.

In additional embodiments of this method, the base is a mounting piece made of rubber or plastic. In embodiments where the base is a mounting piece, the mounting piece may comprise a stabilizing end and the extensions of the base may be tubular. In additional embodiments, the stabilizing end may further comprise a bracket for attaching the mounting piece to a wall or other surface. The stabilizing end can also comprise access openings for each extension. The access openings and extensions can comprise a lead wire removal slit in further embodiments. In embodiments where the base is a mounting piece that comprises a stabilizing end, the glove-like component can also comprise a stabilizer open end adapted to engage with the stabilizing end of the mounting piece.

REFERENCES

The following documents and publications are hereby incorporated by reference.

Other Publications

Hess W, Finck W. Real-time infection protection: using real-time surveillance data, payers and providers are averting infection, saving lives and reaping benefits. Healthc Inform. 2007; 24(8):63-64.
United States Senate. Deficit Reduction Act of 2005. Conference agreement, as amended and passed by the Senate on Dec. 21, 2005.
Barnett T E. The not-so-hidden cost of surgical site infections. AORN J. 2007; 86(2): 249-258.
Brown D Q. Electrocardiography wires: a potential source of infection. AACN News. 2006; 23(9):12-15.
Maki D G, Brookmeyer P R. A survey of EKG telemetry harnesses as a reservoir of resistant nosocomial pathogens. In: Abstracts of the Interscience Conference on Antimicrobial Agents and Chemotherapy. Washington, D.C.: American Society for Microbiology; 2003. Abstract K-746.
Ghandi H, Sharma S, Gilski D, Beveridge R, Patel P. Investigating electrocardiography lead wires as a reservoir for antibiotic-resistant pathogens [abstract 186]. Circulation. 2008; 117(21):e454.
Albert N M, Hancock K, Krajewski S, et al. Multicenter study on reused ECG wires: are monitored patients at risk for nosocomial infections [slides]
Albert N M. Multicenter study on reused ECG wires: are monitored patients at risk for nosocomial infections [research poster]?
Graybill J R, McGowan J E Jr., Corey L American Society for Microbiology. Antimicrobial resistance prevention initiative—an update: proceedings of an expert panel on resistance. Am J Infect Control. 2007; 35(9):S1-S23.
Carson R T, Larson E, Levy S B, Marshall B M, Aiello A E. Use of antibacterial consumer products containing quaternary ammonium compounds and drug resistance in the community. J Antimicrob Chemother. 2008; 62(5): 1160-1162.

What is claimed is:

1. A protective sheath device for protection of lead wire cables and lead wire cable heads from contamination, comprising:
   a glove-like component having a number of fingers for receiving and protecting the lead wire cables and lead wire cable heads, wherein the fingers have terminal closed ends, and wherein the fingers have an extension length and a gathered length that is less than the extension length; and
   a base having a number of extensions for stabilizing the glove-like component while receiving the lead wire cables,
   wherein the glove-like component is adapted to be placed on the base prior to use to facilitate placement of the lead wire cables, wherein the fingers of the glove-like component are adapted to be placed on the extensions of the base to facilitate placement of the lead wire cables, wherein the fingers of the glove-like component are adapted to be gathered to facilitate placement of the lead wire cables, wherein when the fingers of the glove-like component are gathered the fingers have the gathered length to facilitate placement of the lead wire cables, wherein the fingers of the glove-like component are adapted to be extended to the extension length after placement of the lead wire cables and placement of the lead wire cable heads substantially within the terminal closed ends of the fingers, wherein the fingers are adapted to retain the lead wire cable heads substantially within the terminal closed ends and to retain the lead wire cables substantially throughout the extension length after extension, wherein the base is adapted to be removed after placement of the lead wire cables, and wherein the glove-like component protects the lead wire cables from contamination during use.

2. The protective sheath device of claim 1, wherein the number of fingers is the same as the number of extensions.

3. The protective sheath device of claim 1, wherein the extensions are rounded.

4. The protective sheath device of claim 1, wherein the extensions are flat.

5. The protective sheath device of claim 1, wherein the number of fingers is 3, 5, 6, 10, or 12.

6. The protective sheath device of claim 1, wherein the glove-like component is made of plastic.

7. The protective sheath device of claim 6, wherein the plastic is a thickness that permits the lead wire cable heads to be attached to an external device while the lead wire cables heads are received in the glove-like component.

8. The protective sheath device of claim 1, wherein the base is made of disposable cardboard, plastic or paper.

9. The protective sheath device of claim 1, wherein the base has a thickness of about 1 mm to about 30 mm.

10. The protective sheath device of claim 1, wherein the base is a mounting piece made of reusable rubber or plastic.

11. The protective sheath device of claim 10, wherein the mounting piece comprises a stabilizing end and wherein the extensions are tubular.

12. The protective sheath device of claim 11, wherein the stabilizing end further comprises a bracket for attaching the mounting piece to a wall or other surface.

13. The protective sheath device of claim 11, wherein the stabilizing end further comprises access openings for each extension.

14. The protective sheath device of claim 13, wherein the access openings and extensions further comprise a lead wire removal slit.

15. The protective sheath device of claim 11, wherein the glove-like component further comprises a stabilizer open end adapted to engage with the stabilizing end of the mounting piece.

* * * * *